(12) United States Patent
Boyd et al.

(10) Patent No.: US 9,272,094 B2
(45) Date of Patent: Mar. 1, 2016

(54) DRUG DELIVERY DEVICE

(75) Inventors: Malcolm Boyd, Warwickshire (GB);
Robert Veasey, Warwickshire (GB);
David Plumptre, Worcestershire (GB);
David Sanders, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/141,059

(22) PCT Filed: Dec. 21, 2009

(86) PCT No.: PCT/EP2009/067613
§ 371 (c)(1),
(2), (4) Date: Oct. 22, 2011

(87) PCT Pub. No.: WO2010/072699
PCT Pub. Date: Jul. 1, 2010

(65) Prior Publication Data
US 2012/0037530 A1 Feb. 16, 2012

(30) Foreign Application Priority Data

Dec. 23, 2008 (EP) .................................. 08022328

(51) Int. Cl.
*A61M 5/24* (2006.01)
*A61M 5/32* (2006.01)
(Continued)

(52) U.S. Cl.
CPC ................ *A61M 5/24* (2013.01); *A61M 5/3202* (2013.01); *A61M 5/31525* (2013.01);
(Continued)

(58) Field of Classification Search
CPC . A61M 5/24; A61M 5/3202; A61M 5/31525; A61M 5/31533; A61M 2005/3125; A61M 2005/3126; A61M 2205/6072

USPC ........... 604/189, 92, 197, 199, 232, 256, 263, 604/181
See application file for complete search history.

(56) References Cited

U.S. PATENT DOCUMENTS 5,645,534 A * 7/1997 Chanoch ..................... 604/189
5,957,897 A * 9/1999 Jeffrey ........................ 604/223
(Continued)

FOREIGN PATENT DOCUMENTS

DE 19519147 A1 12/1995
EP 1530979 A1 5/2005
(Continued)

OTHER PUBLICATIONS

Form PCT/IB/326, Notification Concerning Transmittal of International Preliminary Report on Patentability.

*Primary Examiner* — Emily Schmidt
*Assistant Examiner* — Lauren M Peng
(74) *Attorney, Agent, or Firm* — McDonnell Boehnen Hulbert & Berghoff LLP

(57) ABSTRACT

The present invention relates to a drug delivery (5) comprising a housing (10) with a proximal end (28) and a distal end (22), a cartridge holder (14) adapted to retain a cartridge, the cartridge holder (14) being secured to the housing (10) and having an at least partially transparent side wall, and a cap (40) being capable of covering the distal end (22) of the drug delivery device, being rotationally fixed with respect to the housing (10) and comprising a window aperture (44), the window aperture (44) being capable of displaying information revealed by the cartridge holder (14). Furthermore, using a cap (40) for covering the distal end (22) of the drug delivery device (5) is disclosed.

17 Claims, 3 Drawing Sheets

Figure 4A:
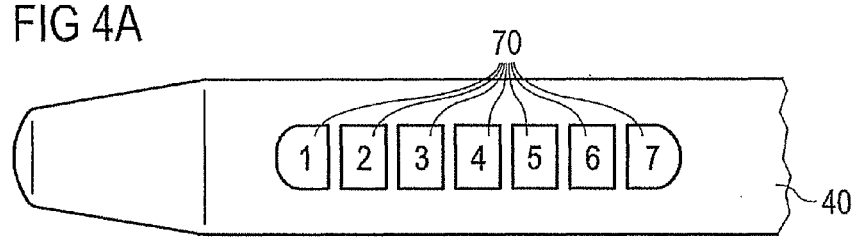

(51) Int. Cl.
*A61M 5/315* (2006.01)
*A61M 5/31* (2006.01)

(52) U.S. Cl.
CPC ... *A61M 5/31533* (2013.01); *A61M 2005/3125* (2013.01); *A61M 2005/3126* (2013.01); *A61M 2205/6072* (2013.01)

(56) References Cited

U.S. PATENT DOCUMENTS

| | | | |
|---|---|---|---|
| 6,120,481 A * | 9/2000 | Rennert et al. | 604/187 |
| 6,491,665 B1 | 12/2002 | Vetter et al. | |
| 7,918,830 B2 * | 4/2011 | Langan et al. | 604/189 |
| 2002/0165500 A1 * | 11/2002 | Bechtold et al. | 604/209 |
| 2005/0113764 A1 * | 5/2005 | Watkins | 604/197 |
| 2008/0108951 A1 * | 5/2008 | Jerde et al. | 604/198 |
| 2008/0269688 A1 | 10/2008 | Colucci et al. | |
| 2008/0306451 A1 * | 12/2008 | Woehr et al. | 604/198 |
| 2010/0016795 A1 * | 1/2010 | McLoughlin | 604/134 |

FOREIGN PATENT DOCUMENTS

| | | |
|---|---|---|
| EP | 1782854 A2 | 5/2007 |
| FR | 2784033 A1 | 4/2000 |
| WO | 9855168 A1 | 12/1998 |
| WO | WO 2008058666 A1 * | 5/2008 |

* cited by examiner

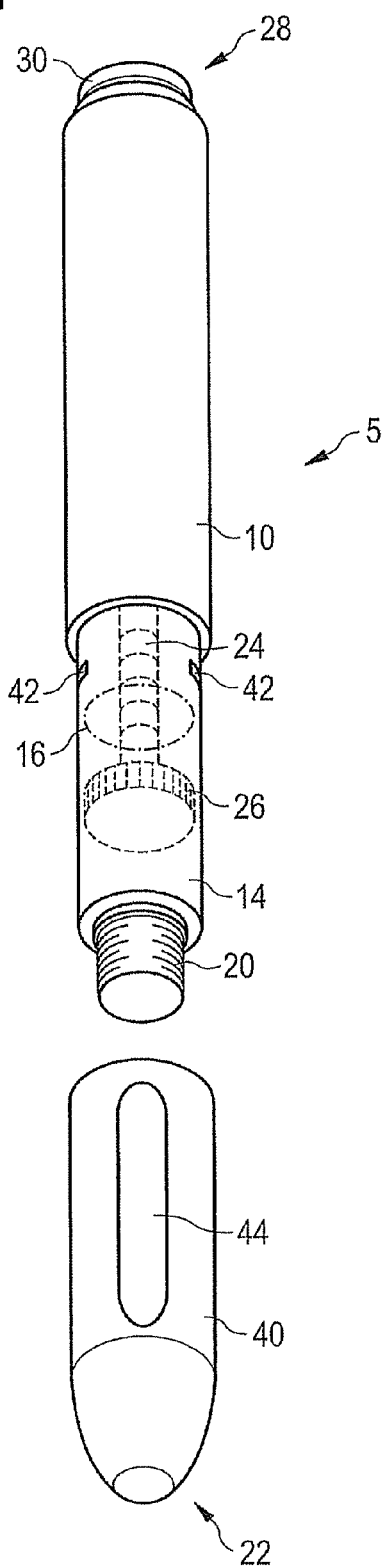

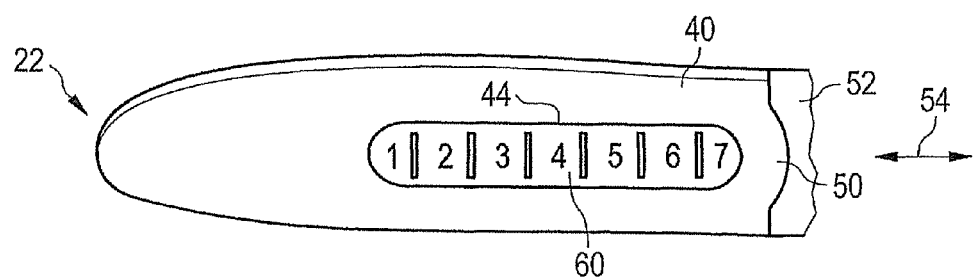
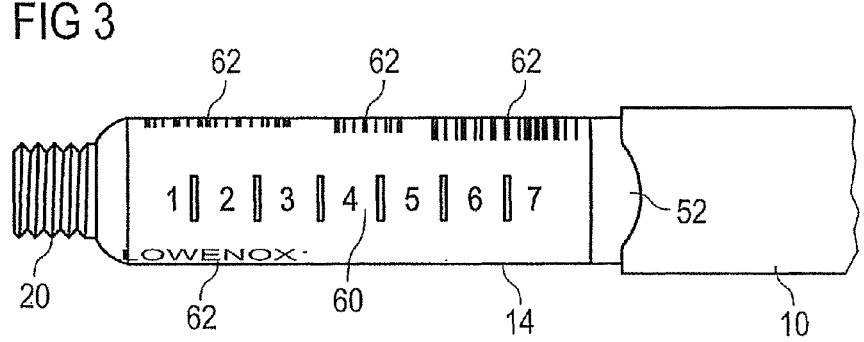

DRUG DELIVERY DEVICE

CROSS REFERENCE TO RELATED APPLICATIONS

The present application is a 35 U.S.C. 371 National Application of PCT/EP2009/067613 filed Dec. 21, 2009 and claims priority to European Patent Application No. 08022328.2, filed Dec. 23, 2008, the entire contents of which are incorporated entirely herein by reference.

The present invention relates to drug delivery devices. Furthermore, the present invention relates to using a cap for covering a distal end of a drug delivery device.

Drug delivery devices are generally known for the administration of a medicinal product, for example insulin, growth hormones or other drugs, in particular medicinal products being suitable for self-administration by a patient.

Some drug delivery devices are configured to deliver a plurality of doses. One particular example of such a drug delivery device is described in the document EP 1 923 084 A1. There, a drug delivery device is shown where a user may activate the drug delivery device. The drug delivery device includes a drive mechanism suitable for use in pen-type injectors, wherein a number of pre-set doses of medicinal product can be administered. A needle unit can be attached to the drug delivery device for dispensing the medicinal product into a patient's skin. After usage of the drug delivery device, the distal end of the device can be covered by a cap.

Additionally, some drug delivery devices are configured to allow setting of different dose sizes which are to be delivered.

It is generally advisable that the drug delivery device is covered by a cap after usage so as to prevent contact with the needle and/or contamination of the device.

In US 2008/0269688 A1 a dose indicating assembly in a pharmaceutical injection device is shown. The dose indicating assembly includes an external housing barrel extending in an axial direction, and a dial at least partially disposed within the housing barrel. The dial is screwably movable in the axial direction relative to the barrel during dose setting. The dial includes an outer radial periphery with a plurality of parallel arrays of dose indicia provided thereon, each of the plurality of arrays of dose indicia provided in a helical pattern on the periphery. The dose indicating assembly also includes means for viewing the dose indicia of a selectively chosen one of the plurality of arrays.

In U.S. Pat. No. 6,491,665 a syringe assembly is shown having a syringe body adapted to be filled with an injectable liquid and having an annular neck defining an axis and having an axially outwardly open outlet. The neck is adapted to carry a needle. An elastomeric plug engaged axially inward with the neck closes the outlet and a holding ring is fixed to the neck below the plug. A retaining sleeve around the neck is fixed to the holding ring and a cup-shaped safety cap is fixed to the plug. The safety cap is formed with at least one radially through going aperture that gives the end user the ability to see if the plug is properly in place before cracking off the cap.

A further injection device with a scale being located on a housing is known from the document DE 298 18 721 U1.

It is an aim of the present invention to provide for an improved drug delivery device. In particular, a drug delivery device should be provided, which allows for an efficient information retrieval by a user before or after operation of the device.

For this aim, a drug delivery device comprises a housing with a proximal end and a distal end, a cartridge holder adapted to retain a cartridge, the cartridge holder being secured to the housing and having an at least partially transparent side wall, and a cap being capable of covering the distal end of the drug delivery device, being rotationally fixed with respect to the housing and comprising a window aperture, the window aperture being capable of displaying information revealed by the cartridge holder.

Thus, the device may comprise at least one window aperture. The window aperture may be configured to be capable of displaying information revealed by the cartridge holder.

The cartridge holder may be permanently or releasably fixed to the housing and thus, reusable or disposable device types are covered by the present disclosure.

In such a drug delivery device, both the cartridge holder and the cap are fixed with respect to the housing. The cartridge holder is covered by the cap on the distal end of the drug delivery device. After engagement of the cap, the cap and the cartridge holder are located at a fixed position with respect to each other. Hence, information revealed by the cartridge holder can be displayed through the window aperture, as no obstruction due to a rotationally moving cap may occur. Information provided on the cartridge holder may be displayed selectively through the at least one window aperture. In particular, information, which may be uninteresting for the user and/or which may be confusing for the user, for example a manufacturing number of the cartridge holder, provided on the cartridge holder axially and/or rotationally offset from the at least one window aperture may be effectively suppressed by means of the cap. Accordingly, crucial information for the user, such as information about the medicinal product contained in the cartridge, may be presented in a clearer and, in particular, in a visually less confusing way.

Furthermore, the cap, the cartridge holder, and the cartridge can be constructed such that the information revealed by the cartridge holder can be imaged through the window aperture, so as to allow a user to quickly gain information regarding the drug delivery device. Consequently, the user can receive information regarding the fill status, the type of medicinal product or the like, even without removing the cap from the drug delivery device. This is in particular useful when a user requires treatment with different medicinal products. According to the invention, a set of drug delivery devices can easily be distinguished from each other by the user without removing the cap from some or all of the devices.

In a first embodiment, the window aperture displays information attached to the cartridge holder.

According to this embodiment, the user can view information which is provided on the cartridge holder. This can include the type of the medical product contained in the cartridge, information being associated with the prescription of the medicinal product or the like. Displaying information through the window aperture is in particular useful when employing the drug delivery device as an expendable product, where usually only one specific medicinal product is dispensed. In this instance it is possible to provide the information on the cartridge holder by means of a label attached to the cartridge holder.

In a further embodiment, the window aperture displays information transmitted from the cartridge through the at least partially transparent side wall of the cartridge holder.

According to this embodiment, information directly attached to the cartridge can be displayed, in particular selectively, through the window aperture. Usually, cartridges can be labeled according to their content. Consequently, the risk of a potential misuse of the drug delivery device is significantly reduced especially when the patient is required to apply different medicinal products. This embodiment is particularly useful where the device is reusable and the user can replace the cartridge, the cartridge in this case containing the information.

Preferably, an orientation feature would ensure that the cartridge could only be assembled to the cartridge holder in one orientation so that the relevant information was visible through the window aperture. Information rotationally and/or axially offset from the position of the window aperture may be effectively suppressed.

In one embodiment, the displayed information represents a type of a drug being contained within the cartridge.

As the type of the drug is permanently displayed, even when the cap is attached to the housing, operation of the medication delivery device is facilitated as the user can gather relevant information at all time without opening the device. Hence, time consuming selection among different devices is no longer necessary, for example.

Furthermore, the window aperture provides a framing of the displayed information as only these parts of the cartridge holder underneath the window aperture are visible for the user. Accordingly, the information is presented in a clearer, i.e. less visually confusing way.

In one embodiment, the displayed information includes a dosage scale.

According to this embodiment, the user is provided with information regarding the filling status of the medication delivery device. This information is in particular useful when the user needs to work through a course of medication that involves a number of disposable drug delivery devices. There, different medication delivery devices are usually contained within a kit. The user may wish to store used and unused devices of the kit within the same compartment, e.g. a box or the like. According to this embodiment, the selection of the correct device is facilitated as filling status information can easily be retrieved through the dosage scale.

In a further embodiment, the cap comprises two window apertures. The window apertures may be arranged angularly offset from each other. The window apertures may be arranged oppositely with respect to each other. One of the window apertures may be arranged to provide information about the medicinal product which information may be revealed by the cartridge holder, for example. The other one of the window apertures may be arranged to provide information about the dosage scale, for example.

In a further embodiment, the dosage scale is printed onto the cartridge holder.

According to this example, the dosage scale can be provided as printed symbols which can be designed for good visibility, e.g. by providing a respective colour which enables a good contrast with respect to the cartridge holder.

In a further embodiment, the dosage scale is moulded onto the cartridge holder.

In this example, the dosage scale can be provided already during manufacturing of the cartridge holder, e.g. by injection moulding. This reduces the number of necessary manufacturing steps and thus may lead to a reduction in manufacturing costs.

In a further embodiment, at least one symbol is printed onto the cap so as to provide further information relating to the dosage scale.

According to this embodiment, attention of the user is attracted as the dosage information can be related to further information, e.g. imminent emptiness of the cartridge contained in the drug delivery device. Hence, operability of the drug delivery device is enhanced.

In a further embodiment, at least one symbol is moulded onto the cap so as to provide further information relating to the dosage scale.

In this example, further information can be provided already during manufacturing of the cap, e.g. by injection moulding. This reduces the number of necessary manufacturing steps and thus may lead to a reduction in manufacturing costs.

In a further embodiment, the drug delivery device comprises a piston rod, the piston rod being adapted to drive a piston so as to advance the piston into the cartridge, the position of the piston within the cartridge being visible through the window aperture.

As the drug is dispensed from the drug delivery device, the piston progressively moves forward towards the distal end of the cartridge. Through the at least partially transparent side wall the position of the piston is visible for the user. Accordingly, the filling status of the drug delivery device can be easily recognized by viewing the piston through the window aperture.

This is in particular useful when the user needs to work through a course of medication that involves a set of disposable drug delivery devices. According to this embodiment, filling status information for each member of the set of disposable drug delivery devices can easily be retrieved through the window aperture. In combination with the dosage scale, the filling status information provided by the position of the piston can even be transferred into a number of doses remaining in the cartridge.

In a further embodiment, the window aperture comprises a plurality of sub-windows.

By sub-dividing the window aperture into a plurality of sub-windows, the information being displayed is framed so as to guide the user in an attempt to retrieve information from the drug delivery device. For example, a first sub window can display information regarding the type of medicinal product contained in the cartridge and a second sub-window can display information regarding the filling status of the device. Accordingly, unnecessary or confusing information which might be present on the cartridge or the cartridge holder can be suppressed by selecting the location of the sub-windows in an appropriate way. Consequently, the framing provided by the sub-windows of the window aperture causes a pre-selection of information to be displayed and the information is presented in a clearer, i.e. less visually confusing way to the user.

In a further embodiment, the sub-windows indicate dosage information as a progressive scale.

In this example, the information regarding the filling status of the drug delivery device is displayed by the advancing piston which progressively moves underneath the corresponding sub-windows of the window aperture. Accordingly, the position of the piston within the cartridge is visible through the partially transparent cartridge holder. Furthermore, the information regarding the filling status is presented in a familiar format to the user which is, for example, similar to a fuel gauge or a battery charge level indicator. Information about the number of doses remaining to be administered from the device can be differentiated from other information on the device and is thus presented in a clear and less confusing manner.

In a further embodiment, the cap is fabricated from an injection moulded plastic.

According to this embodiment, the design of the cap is simplified and conventional techniques can be employed for producing the cap. For example, the cap can be provided as a single injection moulded piece fabricated from thermoplastic materials, e.g. polypropylene, polystyrene, polyamide, polyethylene, or the like.

According to a further embodiment, the cap comprises at least one orientation feature being capable of engaging into a mating orientation feature so as to rotationally fix the cap with respect to the housing. The orientation feature may be configured to be capable of engaging into a mating orientation feature so as to rotationally fix the cap with respect to the housing.

In this example, the cap is rotationally fixed with respect to the housing. Hence, information revealed by the cartridge holder can be displayed through the window aperture, as no obstruction due to a rotationally moving cap may occur.

According to a further embodiment, the cap comprises at least one protrusion serving as an orientation feature, being arranged on an end face of the cap.

In this example, the cap can be implemented such that the protrusion fits into a corresponding part of the housing. Hence, rotationally fixing of the cap with respect to the housing can be provided by the protrusion.

According to a further embodiment, the cap comprises two protrusions which are located at symmetric positions around a longitudinal axis being arranged between the distal end and the proximal end.

In this example, the number of possible orientations of the cap with respect to the housing is reduced which facilitates engaging the cap with the housing. Furthermore, the user is encouraged to place the cap with two possible orientations only. Consequently, an engagement of the cap by the user in arbitrary positions relative to the housing is prevented.

According to a further embodiment, the drug delivery device comprises the at least one orientation feature on the inner side wall of the cap capable of providing guidance when attempting to engage the cap on the housing.

The at least one orientation feature of the cap can be arranged such that it fits into respective grooves on the housing when attempting to engage the cap on the housing. Hence, the orientation feature prevents to place the cap with a false orientation with respect to the housing. Accordingly, only a single orientation of the cap is possible and furthermore the cap is rotationally fixed with respect to the housing.

For the above mentioned aim, a cap is used for covering the distal end of the drug delivery device having a housing with a proximal end and a distal end and with a cartridge holder adapted to retain a cartridge, the cartridge holder being secured to the housing, wherein the cap comprises a window aperture, the window aperture being capable of displaying information revealed by the cartridge holder.

Other features will become apparent from the following detailed description when considered in conjunction with the accompanying drawings.

In the drawings:

FIG. 1 schematically shows a simplified perspective side view of a drug delivery device according to an embodiment;

FIG. 2 schematically shows a simplified side view of a part of a drug delivery device according to an embodiment;

FIG. 3 schematically shows a simplified side view of a part of a drug delivery device according to an embodiment; and FIGS. 4A to 4D schematically show a simplified side view of a part of a drug delivery device according to an embodiment.

In FIG. 1 an embodiment of a drug delivery device 5 is shown, which is an injector for a liquid medication. The drug delivery device may be configured to deliver a plurality of fixed or user-settable doses of a drug. The drug delivery device 5 may be a pen-type device. The drug delivery device 5 comprises a housing 10, which can be formed from a single or from multiple pieces.

In the embodiment shown in FIG. 1, the housing 10 is attached to a cartridge holder 14, wherein a cartridge 16 containing a medical product or drug can be located. The cartridge holder 14 may be secured against movement with respect to the housing 10. The proximal end of the cartridge 16 is indicated by a dashed line in FIG. 1.

A needle unit (not shown in FIG. 1) is located at the distal end 22 of the drug delivery device 5. Through the needle unit the medical product can be injected into a patient. The needle unit can be secured to a needle holder 20 by a threaded engagement. The needle holder 20 forms a part of the cartridge holder 14.

Delivery of the medical product can be performed by means of a piston rod 24, which can be moved in the distal direction with respect to the cartridge 16. A piston 26 which is retained in the cartridge 16 and seals the cartridge on the proximal side 28 may be moved in the distal direction 22 with respect to the cartridge by the piston rod 24. The cartridge holder 14 is fabricated from a transparent or a translucent material, so as to allow viewing of the position of the piston 26 within the cartridge 16.

It should be noted that the description of the drug delivery device 5 as shown in FIG. 1 is merely illustrative. Other elements might be necessary in order to achieve full functionality. For example, a dispense button 30 and a drive mechanism (not shown in FIG. 1) can be present, which are configured to apply the adjusted dose value and move the piston rod and the piston 24 in the distal direction such that the adjusted amount of the medical product is dispensed upon pressing the dispense button 30.

In order to prevent contamination of the drug delivery device 5, a cap 40 is attached to the drug delivery device 5, when the drug delivery device 5 is not in use. The cap 40 covers the distal end 22 of the drug delivery device 5 including the needle holder 20 and the cartridge holder 14. The cap may be a unitary part. The cap 40 may be a single injection moulded piece, for example.

The cap 40 and the cartridge holder 14 can comprise a set of retaining members which are capable of securing the cap 40 with respect to the cartridge holder 14 so as to be rotationally fixed. The retaining member (not shown in FIG. 1) located on the inner surface of the cap 40 is capable of engaging into a corresponding mating retaining member 42 on the cartridge holder 14.

As shown in FIG. 1, the mating retaining member 42 comprises a recess capable of engaging into a corresponding clamp on the cap 40. However, other configurations including, for example, a recess on the cap 40 and a corresponding clamp on the cartridge holder 14 are conceivable as well.

As shown in FIG. 1, the cap 40 includes a window aperture 44. The cap may include two window apertures 44. The two window apertures 44 may be arranged oppositely with respect to each other (not explicitly shown). Through the at least one window aperture 44 information revealed by the cartridge holder 14 can be displayed. As the cartridge holder 14 and the cap 40 are fixed with respect to the housing 10, the cap 40 and the cartridge holder 14 are located at a fixed position with respect to each other after engagement of the cap 40. Information revealed by the cartridge holder 14 can be displayed through the window aperture 44 without being obstructed due to a rotationally moving cap. Furthermore, information provided axially and/or, in particular, rotationally offset from the position of the window aperture 44 may be suppressed by means of the cap 40. The suppressed information may be present but invisible for the user when the cap covers the distal end of the device because the suppressed information is covered by the cap. When the cap is detached, the suppressed information becomes visible and the information contained therein may be retrieved.

Making now reference to FIG. 2, the cap 40 and the distal end of drug delivery device 5 are shown in more detail.

In the embodiment shown in FIG. 2, the cap 40 and the cartridge holder 14 are constructed such that the information revealed by the cartridge holder includes a dosage scale 60, which can be imaged through the window aperture 44. The window aperture 44 is formed in the embodiment shown in FIG. 2 as an elongated slit. However, other forms of the window aperture are conceivable as well, for example rectangular or any other suitable configuration. Furthermore, the cap 40 can also include a further aperture window (not shown in FIG. 2) for displaying further information.

In FIG. 2, the cap 40 comprises a protrusion 50 which is located the proximal end of the cap 40. The protrusion 50 can fit into a corresponding depression 52 on the housing 10. Accordingly, the cap 40 is rotationally fixed with respect to the housing 10 by the protrusion 50, which defines an orientation feature, together with corresponding depression 52 as a mating orientation feature. In this way, information provided on the cartridge holder 14 which is located rotationally offset from the position of the window aperture 44 may be effectively suppressed.

It should be noted that also more than one, for example two protrusions can be arranged at the end face of the cap 40. More specifically, two protrusions can be foreseen at symmetric positions around a longitudinal axis 54 being arranged between the distal end 22 and the proximal end 28 on the cap 40.

Furthermore, the cap 40 can comprise, alternatively or in addition to the protrusion, at least one orientation feature (not shown in FIG. 2) on the inner side wall of the cap 40. The orientation feature is capable of providing guidance when attempting to engage the cap 40 on the cartridge holder 14.

Making now reference to FIG. 3, the cartridge holder 14 on the distal part of drug delivery device 5 is shown in more detail.

In the embodiment shown in FIG. 3, the cartridge holder 14 contains the dosage scale 60 and further information symbols 62 regarding the type of the medicinal product or related to the production of the medical product, e.g. a production date or bar coded production information. It should be noted that part of the information can also be printed on the cartridge 16 and is then transmitted through the transparent side walls of the cartridge holder 14.

As can been seen from FIG. 2 and FIG. 3, the window aperture 44 provides a framing of the displayed information as only these parts of the cartridge holder underneath the window aperture 44 are visible. In the embodiment of FIG. 2 and FIG. 3 only the dosage scale is visible through the window aperture 44 and a user can retrieve fill status information in a clear way without being confused by the further information symbols 62. Also, two oppositely disposed window apertures 44 may be provided on the cap 40 (not explicitly shown). A first window aperture 44 may be arranged to display the dosage scale provided on the cartridge holder 14. Furthermore, the first window aperture 44 may be provided to display the fill status of the cartridge 16. A second window aperture 44 may be arranged to provide information about the medicinal product, like its name, for example.

It should be noted that the invention is not restricted to provide only fill status information. Furthermore, the cap 40 can contain further symbols which provide additional information for the user. For example, letters or numbers can be printed or molded onto the cap 40 (not shown in FIG. 2).

Making now reference to FIGS. 4A to 4D, a further embodiment of the drug delivery device 5 is shown.

In FIGS. 4A to 4D, the position of the piston within the cartridge 16 is visible through the window aperture 44.

As the drug is dispensed from the drug delivery device 5, the piston 26 progressively moves forward towards the distal end 22 of the cartridge 16. Through the at least partially transparent side wall the position of the piston 26 is visible and the filling status of the drug delivery device 5 can be detected by viewing the piston 26 through the window aperture 44.

In combination with the dosage scale 60, the filling status information provided by the position of the piston 26 can be transferred into a number of doses remaining in the cartridge, which is in particular useful for fixed dosage devices.

As shown in FIGS. 4 A to 4D, the window aperture comprises a plurality of sub-windows 70. The sub-windows 70 indicate dosage information as a progressive scale.

The information regarding the filling status is presented as numbers. Information about the number of doses remaining to be administered from the device can be easily retrieved.

Figure 4B:
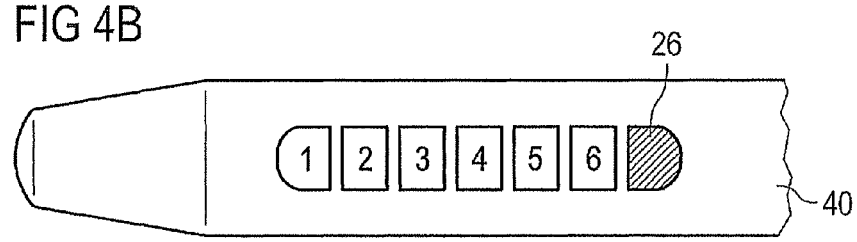
Figure 4C:
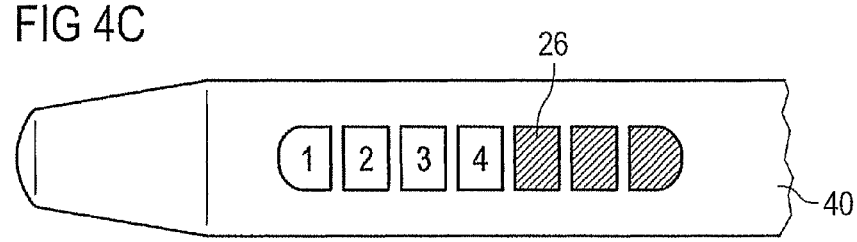
Figure 4D:
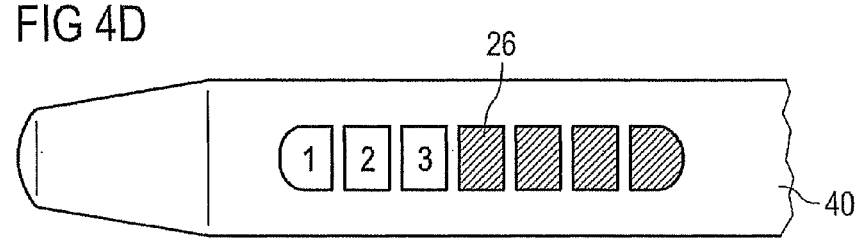

The embodiment of FIG. 4A corresponds to a new device with no dosage dispensed so far. FIG. 4B shows the same device with one dosage applied, i.e. with six dosages remaining. FIG. 4C shows the device after three applied and FIG. 4D after four applied dosages.

Other implementations are within the scope of the following claims. Elements of different implementations may be combined to form implementations not specifically described herein.

REFERENCE NUMERALS

Drug delivery device 5
Housing 10
Cartridge holder 14
Cartridge 16
Needle holder 20
Distal end 22
Piston rod 24
Piston 26
Proximal end 28
Dispense button 30
Cap 40
Mating retaining member 42
Window aperture 44
Protrusion 50
Depression 52
Longitudinal axis 54
Dosage scale 60
Symbols 62
Sub-window 70

The invention claimed is:

1. A drug delivery device comprising:
a housing with a proximal end and a distal end,
a cartridge holder adapted to retain a cartridge, the cartridge holder being secured to the housing and having an at least partially transparent side wall, and
a removable cap that completely covers a distal end of the drug delivery device, and that must be removed before the drug delivery device can be used to inject a dose of medication,
the cap rotationally fixed with respect to the housing and the cap comprising a window aperture, the window aperture being capable of displaying information revealed by the cartridge holder, wherein the displayed information includes a dosage scale on the cartridge holder;

wherein the cap comprises at least one orientation feature aligned with the window aperture and being capable of engaging into a mating orientation feature defined by the housing and aligned with the dosage scale so as to rotationally fix the cap with respect to the housing and to align the window aperture over the dosage scale.

2. The drug delivery device according to claim 1, wherein the window aperture displays information attached to the cartridge holder.

3. The drug delivery device according to claim 1, wherein the window aperture displays information transmitted from the cartridge through the at least partially transparent side wall of the cartridge holder.

4. The drug delivery device according to claim 3, wherein the cartridge is replaceable and wherein an orientation feature defines the orientation in which the cartridge can be assembled to the cartridge holder.

5. The drug delivery device according to claim 1, wherein the displayed information represents a type of a drug being contained within the cartridge.

6. The drug delivery device according to claim 1, wherein the dosage scale is printed onto the cartridge holder.

7. The drug delivery device according to claim 1, wherein the dosage scale is moulded onto the cartridge holder.

8. The drug delivery device according to claim 1, wherein at least one symbol is printed onto the cap so as to provide further information relating to a dosage scale.

9. The drug delivery device according to claim 1, wherein at least one symbol is moulded onto the cap so as to provide further information relating to a dosage scale.

10. The drug delivery device according to claim 1, comprising a piston rod, the piston rod being adapted to drive a piston so as to engage the piston into the cartridge, the position of the piston within the cartridge being visible through the window aperture.

11. The drug delivery device according to claim 1, wherein the window aperture comprises a plurality of sub-windows.

12. The drug delivery device according to claim 11, wherein the sub-windows indicate dosage information as a progressive moving scale.

13. The drug delivery device according to claim 1, wherein the cap is fabricated from an injection moulded plastic.

14. The drug delivery device according to claim 1, wherein the cap comprises at least one protrusion as the orientation feature, the at least one protrusion being arranged on an end face of the cap.

15. The drug delivery device according to claim 14, wherein the cap comprises two protrusions which are located at symmetric positions around a longitudinal axis being arranged between the distal end and the proximal end.

16. The drug delivery device according to claim 1, wherein the cap comprises the at least one orientation feature on the inner side wall of the cap capable of providing guidance when attempting to engage the cap on the housing.

17. Method for covering a distal end of a drug delivery device with a housing with a proximal end and a distal end and with a cartridge holder adapted to retain a cartridge, the cartridge holder being secured to the housing, the method comprising the step of attaching a cap to the drug delivery device for covering the distal end of the drug delivery device when the device is not in use, wherein the cap comprises a window aperture, the window aperture being capable of displaying information revealed by the cartridge holder, and wherein the displayed information includes a dosage scale on the cartridge holder; and wherein the cap comprises at least one orientation feature aligned with the window aperture and being capable of engaging into a mating orientation feature defined by the housing and aligned with the dosage scale so as to rotationally fix the cap with respect to the housing and to align the window aperture over the dosage scale.

* * * * *